United States Patent [19]

Keranen

[11] Patent Number: 5,662,702
[45] Date of Patent: Sep. 2, 1997

[54] INTRAVASCULAR GRAFT AND CATHETER

[76] Inventor: Victor J. Keranen, 410 Murray Hill Rd., Fayetteville, N.C. 28303

[21] Appl. No.: 698,449

[22] Filed: Aug. 30, 1996

Related U.S. Application Data

[63] Continuation of Ser. No. 425,833, Apr. 20, 1995, Pat. No. 5,609,628.

[51] Int. Cl.$^6$ .................................................. A61F 2/06
[52] U.S. Cl. .................................................. 623/1; 623/12
[58] Field of Search .................................. 623/1, 11, 12; 606/108, 191, 194, 195, 198; 604/96, 104, 281

[56] References Cited

U.S. PATENT DOCUMENTS

| Re. 32,348 | 2/1987 | Pevsner | 606/194 |
|---|---|---|---|
| 2,259,488 | 10/1941 | Raiche | 604/281 |
| 4,190,909 | 3/1980 | Ablaza | 3/1.4 |
| 4,313,231 | 2/1982 | Koyamada | 3/1.4 |
| 4,502,159 | 3/1985 | Woodroof et al. | 623/1 |
| 4,562,596 | 1/1986 | Kornberg | 623/1 |
| 4,577,631 | 3/1986 | Kreamer | 128/334 |
| 4,617,932 | 10/1986 | Kornberg | 128/334 |
| 4,740,207 | 4/1988 | Kreamer | 623/12 |
| 4,877,030 | 10/1989 | Beck et al. | 623/1 |
| 4,878,906 | 11/1989 | Lindemann et al. | 623/1 |
| 5,078,726 | 1/1992 | Kreamer | 606/194 |
| 5,156,620 | 10/1992 | Pigott | 623/1 |
| 5,207,695 | 5/1993 | Trout, III | 606/153 |
| 5,211,658 | 5/1993 | Clouse | 623/1 |
| 5,258,042 | 11/1993 | Mehta | 623/66 |
| 5,282,824 | 2/1994 | Gianturco | 606/198 |
| 5,509,902 | 4/1996 | Raulerson | 623/11 |
| 5,522,840 | 6/1996 | Krajicek | 623/12 |

FOREIGN PATENT DOCUMENTS

| 0 508 473 A2 | 10/1992 | European Pat. Off. . | |
| 9324075 | 12/1993 | WIPO | 623/12 |

OTHER PUBLICATIONS

Cragg et al.; Percutaneous Arterial Grafting, *Radiology* 150:45–49 (1984).

Wright et al.; Percutaneous Endovascular Stents: An Experimental Evaluation, *Radiology* 156:69–72 (1985).

Mirich et al.; Percutaneously Placed Endovascular Grafts for Aortic Aneurysms: Feasibility Study, *Radiology* 17:1033–1037 (1989).

*Primary Examiner*—Randy C. Shay
*Attorney, Agent, or Firm*—Bell, Seltzer, Park & Gibson

[57] ABSTRACT

An intravascular graft for restoring normal blood flow in vessels, or for defining new blood flow pathway in arteries includes a proximal collar to aid in anchoring the graft in place. The graft may contain defects in the graft wall to allow blood flow therethrough. Struts encircling the graft provide structural stability. Additional elements which aid in anchoring the graft in place include barbed collars and graft walls which contain ridges. Additional elements to aid in placement include a drawstring associated with the graft collar. A graft designed for use with vessels configured similarly to the basilar artery contains a cap at the distal end of the graft. A catheter to facilitate placement of intravascular grafts is also disclosed.

2 Claims, 4 Drawing Sheets

INTRAVASCULAR GRAFT AND CATHETER

This application is a continuation of application Ser. No. 08/425,833 filed Apr. 20, 1995, now U.S. Pat. No. 5,609,628.

FIELD OF THE INVENTION

The present invention relates to the field of intravascular repair and, more particularly, relates to intravascular grafts and catheters for use in treating damaged or diseased arterial vessels. Intravascular grafts are used to define a new passageway for blood flow, in order to bypass damaged or diseased portions of a vessel. The invention provides an intravascular graft and a device for inserting an intravascular graft into a damaged vessel wherein the graft expands to conform to the vessel walls.

BACKGROUND OF THE INVENTION

Treating damaged arteries to preserve desired blood flow often comprises the placement of a thin-walled tubular device, known as a graft or stent, within the damaged artery. These device are used to treat congenital malformations or acquired abnormalities, such as aneurysms, or for the therapeutic occlusion of selected vessels.

Arterial aneurysms are formed when a section of blood vessel wall, weakened due to age, disease, congenital malformation or trauma, expands in response to the pressure of the existing blood flow to form a bulge or pocket in the arterial wall. The normal pathway of blood flow is interrupted, and the bulging aneurysmal wall is at risk for rupture. Aneurysms may occur in virtually any artery in the body, from the large ascending aorta to smaller cerebrovascular vessels such as the basilar artery.

Other arterial defects which disrupt normal blood flow include arterial dissection, wherein a partial tear of the artery wall allows blood to collect between the layers of the vessel wall and results in bulging of the vessel wall and narrowing of the normal blood flow path. Trauma may rupture blood vessels, allowing the formation of a hematoma around the damaged vessel. The hematoma may form a pseudoaneurysm, which is an aneurysm without a defined vascular wall.

Treatment of the above vascular defects includes re-defining normal blood flow by isolating the aneurysmal area from the normal circulation pathway. Methods of treatment include exposing the aneurysm surgically and ligating the aneurysm with sutures and/or metal clips; investing the aneurysmal pouch with plastic or other materials; and coagulating the contents of the aneurysmal pouch using cautery.

In some situations it may be desirable to define new blood flow pathways. In certain cases the treatment of tumorous growths includes occluding an artery supplying blood to tumor tissue. Fistulas are anomalous connections between an artery and another vessel; obstructing this connection may be required to establish desired blood flow.

SUMMARY OF THE INVENTION

In view of the foregoing, it is therefore an object of the present invention to provide an intravascular graft having an elongate body defining an internal tubular passageway, and having a proximal collar extending generally radially outward from the proximal end of the graft to aid in anchoring the graft in place. Defects (openings or apertures) may be formed in the graft wall to allow blood flow to branching arteries.

A further object of the invention is to provide an intravascular graft having an elongate body defining an internal tubular passageway, a proximal end and a distal end, and having a gap formed in and extending the length of the elongate body. The gap in the elongate body allows the internal diameter of the graft to vary in size. A circumferentially discontinuous, or C-shaped, distal collar extends outward from the distal end of the intravascular graft, and each tip of the C-shaped distal collar has an aperture formed therein. A drawstring is threaded through the apertures, so that pulling on the drawstring brings the tips of the distal collar together, and decreases the diameter of the internal passageway.

A further object of the present invention is an intravascular graft having an elongate body defining an internal tubular passageway, and having a cap affixed to the distal end of the tubular body. The cap has a cross-sectional diameter greater than that of the tubular body, to aid in placing and retaining the graft.

A further object of the present invention is a catheter for use in placing an intravascular graft. The catheter includes an elongate tubular body in which a triangular wedge has been affixed, so that the base of the triangular wedge is substantially aligned with the distal end of the tubular body.

DETAILED DESCRIPTION OF THE PREFERRED EMBODIMENTS

The present invention will now be described more fully hereinafter with reference to the accompanying drawings, in which preferred embodiments of the invention are shown. This invention may, however, may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

The present invention provides a method for reestablishing desired blood flow in vessels without surgically exposing the artery, and particularly provides a method of treating human arteries of small diameter, such as cerebrovascular arteries. Numerous diverse diseases result in abnormal arterial blood flow which may be suitable for treatment using the device and method of the present invention, as will be apparent to those skilled in the art.

Proximal and distal are used herein in relation to normal blood flow. Thus in an artery containing an intravascular graft according to the present invention, blood enters the proximal end of the graft and exits the distal end.

Figure 1:
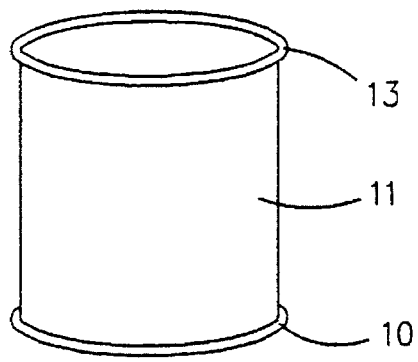
FIG. 1 is a side view of an intravascular graft according to the invention, showing proximal and distal collars extending from the graft wall.

FIG. 1 illustrates an intravascular graft of the present invention having a flexible wall 11 which defines an internal tubular passageway, a proximal end and a distal end, and an inner and outer surface. A projection extending generally radially outward from the proximal end of the intravascular graft forms proximal collar 10 having a diameter slightly greater than that of graft wall 11. Both tubular graft wall 11 and proximal collar 10 are made of flexible material and, when placed in a vessel, bulge outward in response to the pressure of blood flow. In treating a selected vessel, the wall 11 of the intravascular graft had an external diameter of a size sufficient to form an interference fit with the internal wall of the vessel. Proximal collar 10, being of slightly greater diameter than the tubular wall, also forms an interference fit with the internal vessel wall to help prevent migration or embolization of the graft after placement in the vessel. The graft is placed in the vessel so that blood enters the graft at the proximal end and exits from the distal end. An optional distal collar 13 may be formed on the distal end of the intravascular graft.

Figure 2:
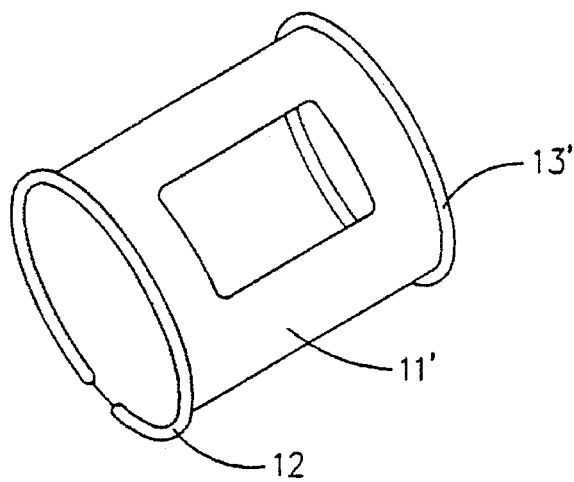
FIG. 2 is a perspective view of an intravascular graft according to the invention having a circumferentially discontinuous proximal collar and a defect formed in the graft wall.

FIG. 2 illustrates an intravascular graft having a discontinuous proximal collar 12, i.e., having a gap or defect therein so that proximal collar 12 is C-shaped. The gap allows proximal collar 12 to expand in response to normal blood pressure, in addition to the expansion provided by the flexibility of the material used to construct proximal collar 12. An optional distal collar 13' may be formed on the distal end of the intravascular graft, and may be continuous or discontinuous.

Figure 3:
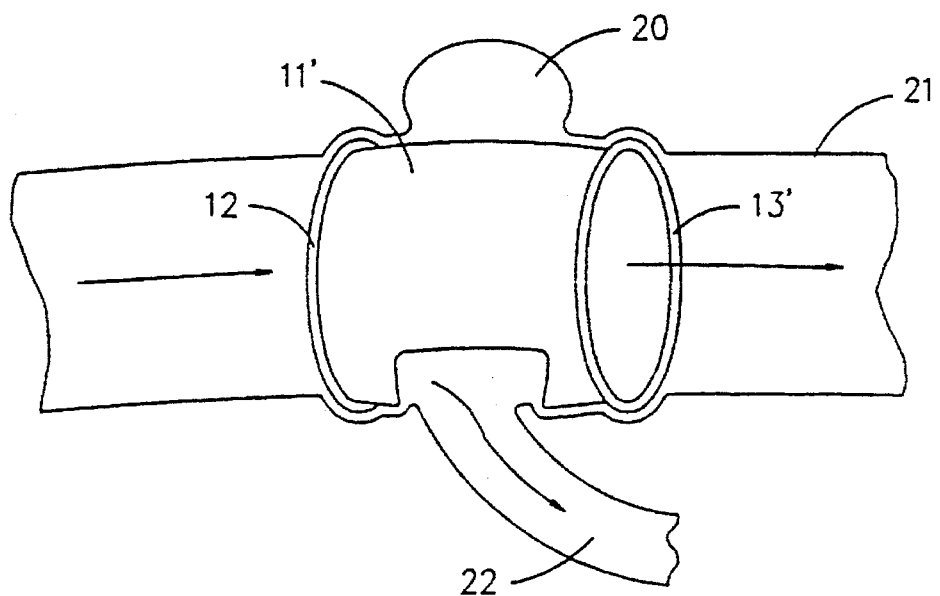
FIG. 3 is a schematic fragmentary view of an intravascular graft according to the present invention positioned within an aneurysmal blood vessel. Arrows indicate the flow of blood.

FIG. 2 further illustrates an intravascular graft in which graft wall 11' has an opening or defect formed therein. Use of such a graft is shown in FIG. 3 (arrows indicate the direction of blood flow). The graft is placed such that graft wall 11' isolates aneurysmal pouch 20 from the artery and establishes blood flow along a path similar to that which occurred prior to the formation of the aneurysm. The defect in graft wall 11' is positioned to allow continued normal blood flow to branching artery 22. As used herein, defect means an aperture or opening. Defects formed in wall 11' of the graft may take the form of a single aperture, an aperture interrupted by structural elements (such as struts 33, described below), or a plurality of apertures. The size and position of defects in graft wall 11' will vary with the anatomy of the vessel being treated, as will be apparent to one skilled in the art.

As shown in FIG. 3, proximal collar 12 and distal collar 13' and flexible graft wall 11' bulge outward in response to normal blood pressure, so that the blood path defined by the graft is of slightly larger diameter than the blood path defined by internal blood vessel wall 21 proximal to or distal to the graft. The bulging of the intravascular graft aids in anchoring the graft in place.

Figure 4:
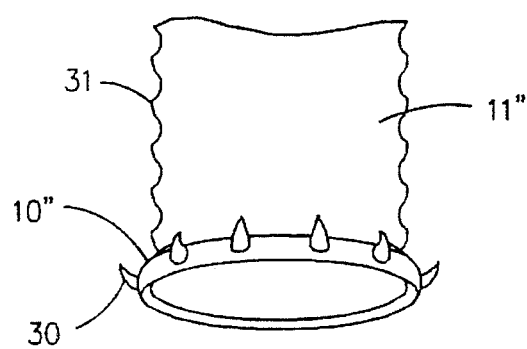
FIG. 4 is a fragmentary view of an intravascular graft according to the present invention having barbs extending radially outward and distally from the proximal collar, and having a plurality of raised ridges on the exterior surface of the graft.

The graft of the present invention may include additional structural elements which aid in the placement and anchoring of the graft. As shown in FIG. 4, proximal collar 10" may have placed thereon barbs or hooks 30 which extend radially outward from proximal collar 10" and are curved or angled distally (i.e., in the direction of normal blood flow when the graft is placed within a vessel). In use, the force of the blood flow assists in anchoring barbs 30 into the internal wall of the blood vessel. Once anchored, the barbs hold the graft in place. Distal collars may similarly have distally-angled barbs or hooks placed thereon to aid in anchoring the graft. As also shown in FIG. 4, the outer surface of graft wall 11" may have formed thereon ripples or ridges 31 to aid in anchoring the graft by friction against the internal vessel wall. The inner surface of intravascular graft wall 11' is, however, preferably smooth to facilitate the growth of the intima (the innermost layer of the blood vessel, also known as the tunica intima) within the graft. In use it is desirable that the interior of the intravascular graft be overgrown by the intima, to provide a passageway similar to the natural artery. This growth is facilitated by a smooth inner surface of the intravascular graft.

Figure 5:
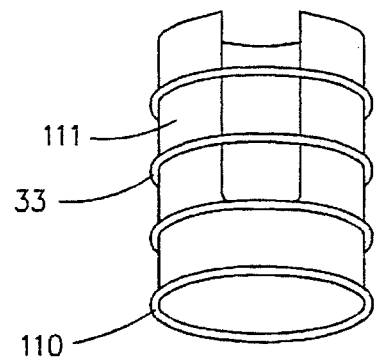
FIG. 5 is a fragmentary view of an intravascular graft according to the present invention having circular struts attached to the graft wall and spanning a defect formed in the graft wall.

As illustrated in FIG. 5, the intravascular graft may have a plurality of generally circular ribs or struts 33 encircling graft wall 111. Struts 33 may be affixed to the exterior of graft wall 111 such that they form ridges thereon, and may be made of the same material as the tubular wall or a different material. In an alternative embodiment, struts 33 are disposed within graft wall 111 and are made of a material different than graft wall 111 which imparts increased rigidity to the graft wall 111. For example, the struts may be disposed within graft wall 111 and made of a less flexible material.

As further shown in FIG. 5, in grafts containing a defect in graft wall 111, struts 33 span the defect to impart structural stability to graft wall 111 and the edges of the defect, while allowing blood to flow through the defect essentially unimpeded.

Figure 6:
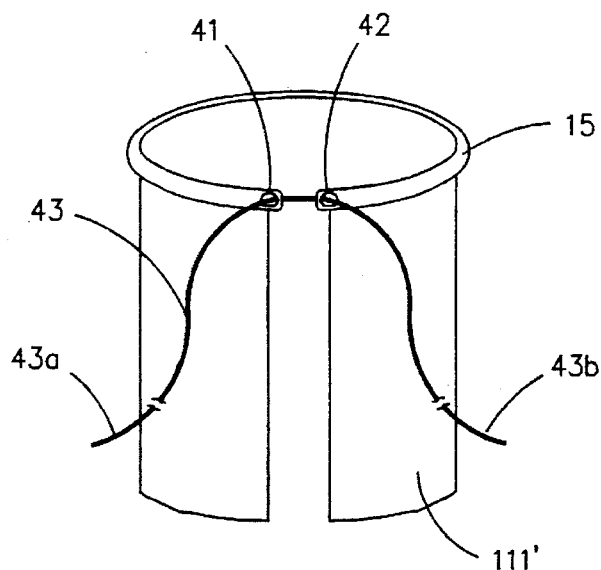
FIG. 6 is a fragmentary view of an intravascular graft according to the present invention having a longitudinal slit or aperture extending the length of the graft wall, and having a circumferentially discontinuous distal collar with a drawstring attached thereto.

As illustrated in FIG. 6, in another embodiment the graft comprises an essentially rectangular sheet of flexible material which is curved or rolled so that two parallel sides of the rectangular sheet oppose each other to form an elongate tubular body defining an internal passageway, having a proximal end and a distal end, an inner surface and an outer surface, and having a slit or opening extending the length of the elongate tubular body. Described in another way, the graft is a tubular graft having a slit or opening formed in graft wall 11 and extending the complete length of the tubular graft. In use, the graft is placed with the slit or opening abutting healthy blood vessel wall, so that blood flow occurs along a pathway defined by the graft wall 111' and the healthy wall of the artery. The slit allows the graft to expand and increase the diameter of the internal passageway, to accommodate arteries of differing sizes.

The graft may further comprise a drawstring to aid in placement of the graft within a blood vessel. As shown in FIG. 6, the graft comprises a discontinuous, or C-shaped, distal collar 15 having first tip 41 having a first aperture formed therein and second tip 42 having a second aperture formed therein. The gap in distal collar 15 is aligned with the slit in graft wall 111'. A drawstring 43 having a first end 43a and a second end 43b is threaded through the aperture formed in first tip 41 and the aperture formed in second tip 42. During placement of the graft, pulling on the ends of the drawstring draws the opposing edges of distal collar 15, and hence graft wall 111', together to reduce the overall diameter of the graft and facilitate manipulation and placement of the graft in the artery being treated. Once the graft is placed, drawstring 43 is removed by pulling on one end of drawstring 43.

Figure 7:
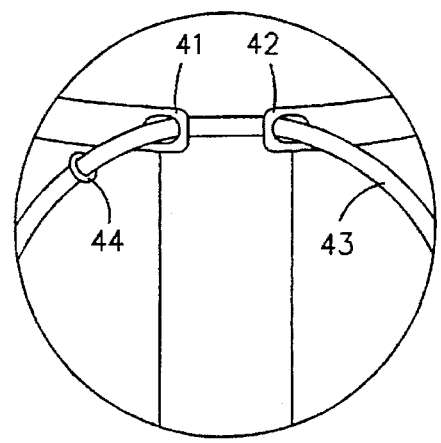
FIG. 7 is an enlarged fragmentary view of the distal collar of FIG. 6, showing the drawstring extending through apertures in the tips of the distal collar.

As illustrated in FIG. 7, drawstring 43 may include a protrusion 44 located intermediate first end 43a of the drawstring and first collar tip 41. In this embodiment, only second end 43b of the drawstring needs to be pulled to bring the opposing edges of the graft together, as protrusion 44 pushes against first collar tip 41. Removal of drawstring 43 is accomplished by pulling on first end 43a. It will be apparent to one skilled in the art that protrusion 44 may be of various shapes, as long as it is capable of transmitting force to the distal collar.

Figure 8:
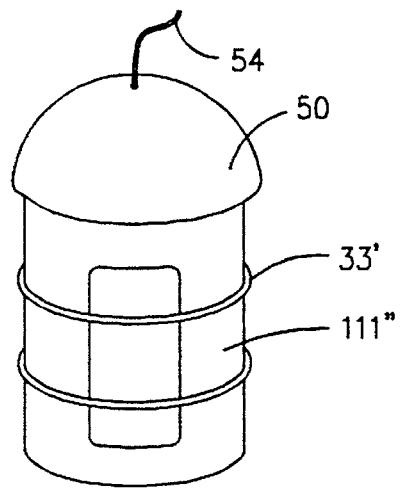
FIG. 8 is a side view of an intravascular graft according to the present invention having a hemispherical cap attached to the distal end of the graft, and having a defect formed in the tubular wall of the graft.
Figure 9:
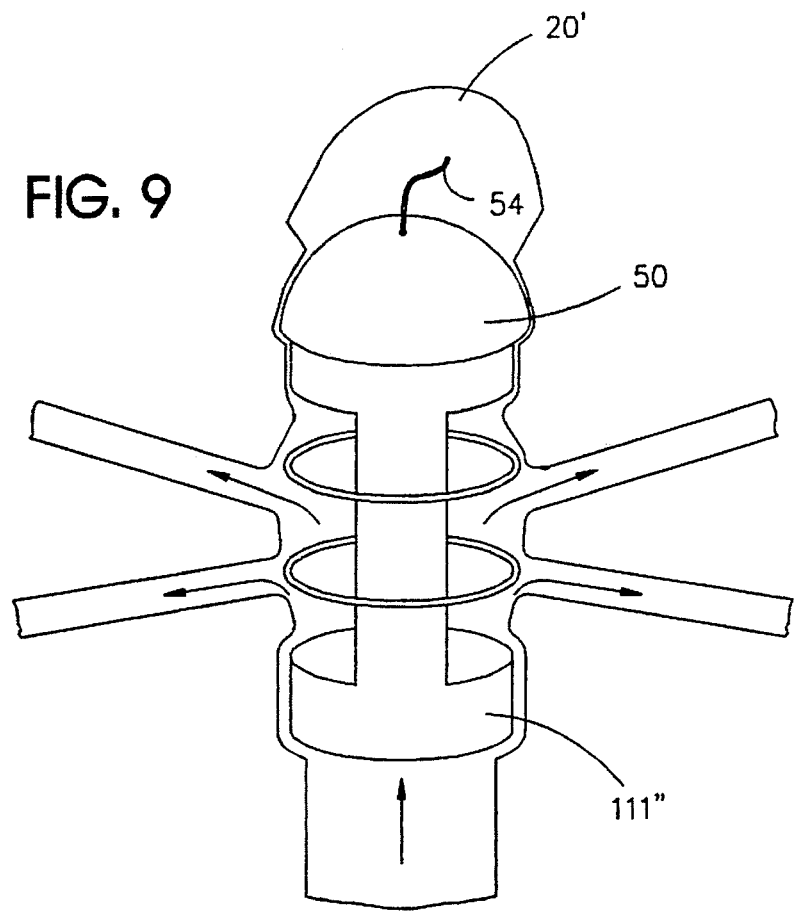
FIG. 9 is a cut-away schematic view of the intravascular graft of FIG. 8 positioned in a basilar artery aneurysm.

FIG. 8 depicts an intravascular graft designed for the treatment of aneurysms in vessels with configurations similar to that of the basilar artery. The basilar artery is a cerebral vessel terminating in four laterally branching arteries, two arising from each side of the basilar artery. As shown in FIG. 9, basilar artery aneurysm pouch 20' commonly forms in the distal tip of the basilar artery. As shown in FIG. 8, one embodiment of the present intravascular graft comprises an essentially tubular graft having a proximal end and a distal end, and an inner and outer surface, and cap 50 having opposite proximal and distal cap ends. Cap 50 has a generally round cross-sectional shape. The proximal end of cap 50 is attached to the distal end of the graft. Cap 50 may be solid or hollow, but if hollow, the interior of cap 50 is not in fluid communication with the internal passageway of the graft, to prevent blood flow into cap 50. The cross-sectional diameter of cap 50 is larger than that of the graft, to aid in anchoring the graft in place. Cap 50 may be generally cylindrical. In a preferred embodiment the distal end of cap 50 is rounded, as provided by spherical or hemispherical caps. FIG. 8 depicts a graft having a hemispherical cap 50; the proximal surface of the hemispherical cap is attached to the distal end of the graft. When cap 50 is hemispherical, the proximal cap surface may be planar or may be concave. A filament or thread 54 may optionally be attached to distal surface of cap 50. In use, filament 54 extends into the interior of the aneurysmal pouch to promote coagulation therein.

Defects or openings formed in the graft wall 111" of the graft, of a number and dimension such that when the graft is placed within the vessel being treated, blood flow is preserved to each laterally branching artery. In treating a basilar artery aneurysm, for example, two defects are formed in the graft wall essentially opposite one another. The graft may include generally circular struts 33' which span the defects in graft wall 111" to impart structural stability to the graft while allowing blood flow through the defects. In addition to providing structural stability, struts 33' may be formed such that they protrude from the outer surface of graft wall 111" to provide ridges which aid in holding the graft in place, as discussed above.

FIG. 9 shows an intravascular graft of the present invention used to treat a basilar artery aneurysm (arrows indicate the direction of blood flow). Cap 50 of the graft extends into aneurysmal pouch 20'. Filament 54, attached to hemispherical cap 50, extends into the interior of aneurysmal pouch 20'. The graft is placed such that the graft wall 111" abuts the wall of the basilar artery, while the defects in graft wall 111" correspond to the laterally branching arteries.

The intravascular grafts of the present invention are sized according to the diameter of the vessel in which they are to be used, as would be apparent to one skilled in the art. In general, the external diameter of the tubular graft wall is of a size sufficient to form an interference fit with the internal wall of the vessel being treated. Length of the graft will vary depending on the condition being treated, as will be apparent to one skilled in the art. In general, the internal diameter of intravascular grafts according to the present invention range from about 4 centimeters to about 0.5 millimeters, more preferably range from about 2 centimeters to about 1.0 millimeter, and most preferably range from about 1 centimeter to about 1 millimeter. For treating conditions in cerebral vessels, such as basilar artery aneurysms, the internal diameter of the grafts are preferably from about 6 millimeters to about 0.5 millimeter, more preferably are from about 4 millimeters to about 1 millimeter, and most preferably are from about 4 millimeters to about 2 millimeters.

Intravascular grafts of the present invention may be used to treat aneurysms in vessels including, but not limited to, the brachio-cephalic artery, carotid artery, coronary arteries, vertebral artery, cerebral arteries including the basilar artery, the femoral artery, popliteal artery, iliac artery, abdominal aorta, the portacaval system, splenic artery, gastric artery, hepatic artery and superior and inferior mesenteric artery.

A further aspect of the present invention is a catheter used to facilitate placement of intravascular grafts. Intravascular catheters are known in the art for use in a variety of therapeutic and diagnostic techniques, and are typically inserted into and guided through the vascular system until the treatment site is reached. When used to place intravascular grafts, a catheter carrying the intravascular graft is inserted into the vascular system at an accessible site and guided through the vascular system to reach the treatment site, where the intravascular graft is expelled from the catheter. The catheter is then removed from the vascular system, leaving the intravascular graft in place.

Figure 10:
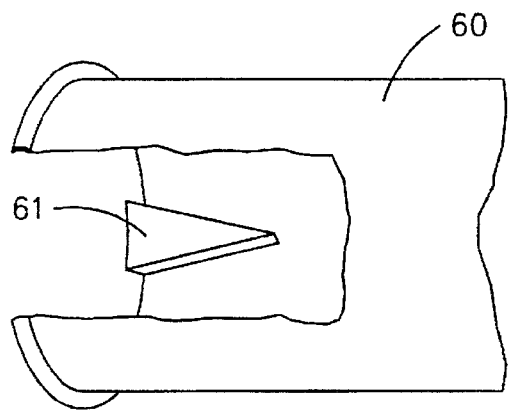
FIG. 10 is a partially cut-away view of a catheter according to the present invention, showing the triangular wedge attached to the interior wall of the catheter.

As shown in FIG. 10, the catheter of the present invention comprises an elongate flexible tube 60 having a distal end and a proximal end, and an internal wall and an external wall. The tube is sized so that an intravascular graft may be carried within its lumen and so that the catheter may reach the treatment site, as is known in the art. At the distal end of flexible tube 60 a triangular wedge 61 is attached to the internal wall of the tube, with the base of triangular wedge 61 substantially aligned with the distal end of the tube and the apex extending proximally through the tube. The height of wedge 61 may be uniform, that is, the same at the base and apex as shown in FIG. 10, or wedge 61 may slope from apex to base. The flexible tube 60 of the catheter may optionally have a plurality of generally circular ribs or struts encircling the tubular catheter wall to add stability thereto. Struts may be made of the same material as the tubular wall or a different biocompatible material.

Figure 11:
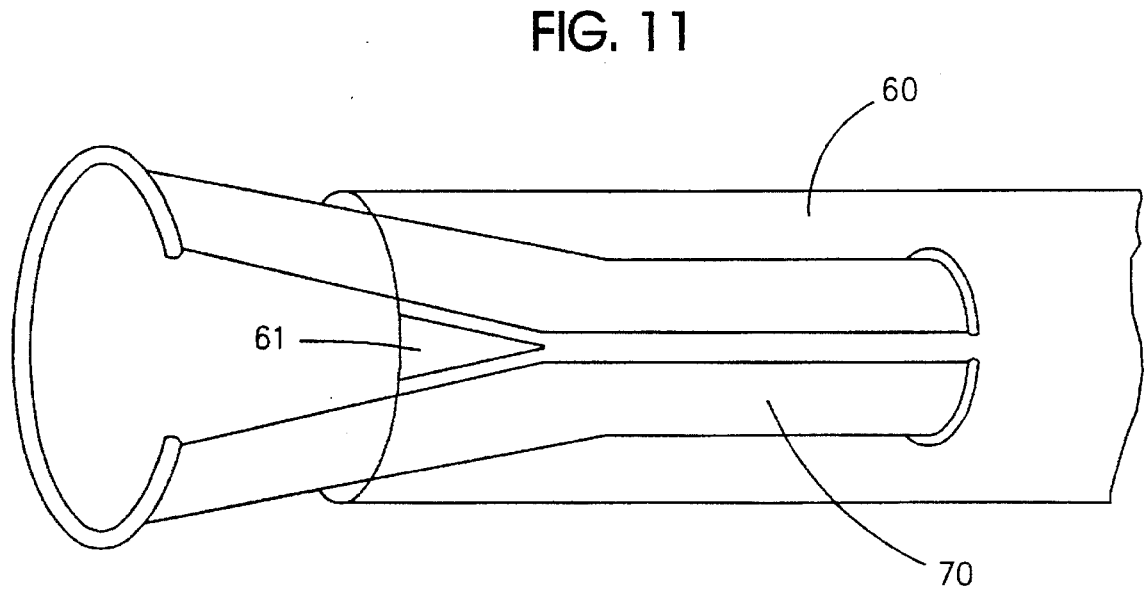
FIG. 11 is a schematic drawing showing the catheter of FIG. 10 in use, wherein an intravascular graft is expelled from the distal end of the catheter.

The catheter of FIG. 10 is designed for use with intravascular grafts as shown in FIGS. 6 and 7, wherein a slit or defect extends the length of the graft wall. In use, as shown in FIG. 11, the intravascular graft 70 is disposed within the catheter with the slit aligned with the apex of triangular wedge 61. When the catheter has been properly positioned at the treatment site, the graft is expelled from the catheter. Triangular wedge 61 forces the opposing edges of intravascular graft 70 apart and thereby increases the diameter of intravascular graft 70. In this manner a catheter smaller in diameter than the vessel being treated can be used to deliver an intravascular graft of sufficient size for the vessel being treated.

Intravascular grafts and catheters according to the present invention may be formed of any flexible, biocompatible, nonthrombogenic material which can be molded or shaped to the appropriate diameter and configuration. Suitable materials will possess sufficient flexibility to respond to the pressure exerted by blood flow, but will possess sufficient rigidity to avoid prolapsing into an aneurysmal pouch. Suitable materials include, but are not limited to, silicone, polytetrafluoroethylene (Dacron® or Gore-Tex®), Teflon®, and expanded polytetrafluoroethylene (ePTFE). The material should be biologically inert and compatible with the tissues into which the graft is placed, as is known in the art, and the surface of the material may be treated to increase bio-compatibility, as is known in the art.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. An intravascular graft comprising: an elongate body having a flexible wall defining a tubular passageway, and opposite proximal and distal ends, and having a gap formed in and extending the length of said elongate body;

a proximal collar extending generally radially outwardly from said body proximal end;

a distal collar extending generally radially outwardly from said body distal end having a first tip and a second tip, said first tip having a first aperture formed therein and said second tip having a second aperture formed therein; and a removable drawstring having a first end and a second end, said drawstring passing through said first aperture and said second aperture.

2. An intravascular graft according to claim 1, further comprising a projection extending radially from said removable drawstring and positioned between an end of said drawstring and one of said first and second tips.

* * * * *